United States Patent [19]

Layton

[11] Patent Number: 4,804,376
[45] Date of Patent: Feb. 14, 1989

[54] ANNULAR REFLUX INDICATOR FOR A URINE COLLECTION BAG

[75] Inventor: Terry Layton, Arlington Heights, Ill.
[73] Assignee: The Kendall Company, Boston, Mass.
[21] Appl. No.: 126,334
[22] Filed: Nov. 30, 1987
[51] Int. Cl.$^4$ .............................................. A61M 1/00
[52] U.S. Cl. .................................................. 604/318
[58] Field of Search ............... 604/318, 324, 335, 350, 604/323; 128/760, 767, 766, 771; 604/318, 322–324, 335, 350, 361, 404

[56] References Cited

U.S. PATENT DOCUMENTS

| | | | |
|---|---|---|---|
| 3,626,980 | 12/1971 | Svensson | 604/323 |
| 3,838,691 | 10/1974 | Paludan et al. | 604/324 |
| 4,512,770 | 4/1985 | Cianci et al. | 604/335 |
| 4,521,213 | 6/1985 | Steigerwald | 604/335 |
| 4,693,712 | 9/1987 | Bates | 604/323 |

Primary Examiner—Stephen C. Pellegrino
Assistant Examiner—J. L. Kruter
Attorney, Agent, or Firm—Donald N. Halgren

[57] ABSTRACT

A reflux indicating device for a urine collection bag which has a chamber for collecting urine from a patient. A receiving conduit is in communication with the drain tube on a catheter to empty urine into the chamber. An annular channel is secured into the upper distal most end of the receiving conduit. If the bag is laid on one of its sides, urine will get trapped in the channel and alert medical personnel of possible retrograde contamination of the drain tube and catheter by bacteria contained within any urine already in the chamber.

6 Claims, 1 Drawing Sheet

ANNULAR REFLUX INDICATOR FOR A URINE COLLECTION BAG

BACKGROUND OF THE INVENTION (1) Field of the Invention

This invention relates to urine collection bags and more particularly to a reflux indicator arranged onto the inlet part of a urine collection bag.

(2) Prior Art

Urine collection from a patient usually involves catheterization wherein a catheter is placed in the patient such that it communicates with the patient's bladder, and during catheterization urine drains from the bladder through the catheter and a drainage tube to the collection bag for retention therein. Such systems should be closed to the atmosphere to minimize the possibility of contamination. Nonetheless, a persistent problem remains, in that the collected urine in the bag may become contaminated, which could result in undesirable retrograde bacteria movement through the system to the bladder of the patient.

Urine bags for this reason, should always be kept below the patient's bladder. Some collection bags have anti-reflux valves in their flowpaths to prevent or minimize the likelihood of reflux of urine from the bag to the bladder if the bag is tipped or if the bag is inadvertently placed above the bladder.

An anti-reflux valve of this type is shown in U.S. Pat. No. 4,490,144 to Steigerwald, wherein a disc member is movably closable against an aperture, when its containment bag is improperly moved.

It is desirable however, to have a collection bag which will indicate if it actually has been improperly tipped, any anti-reflux system notwithstanding.

Thus, it is an object of the present invention to provide a reflux indicator in the fill system, to provide a signal to appropriate medical personnel that the bag has been tipped, and that appropriate action may have to be undertaken. The reflux indicator also tends to discourage mishandling of the collection bag by medical personnel who might otherwise tend to rely on an anti-reflux valve.

BRIEF SUMMARY OF THE INVENTION

The present invention comprises a collection bag for the receipt and containment of body fluids such as urine. The bag includes a hollow connector portion which extends from a drainage tube connected to a catheter attached to a patient. The hollow connector portion includes a drip chamber which is in fluid communication through an inlet port, with the collection bag.

The drip chamber is a tubular member, normally in a vertical orientation in use with a patient. The inlet port is an L-shaped member which provides fluid communication between the drip chamber and the drainage bag. The drip chamber extends into the inlet port and terminates therein, in a diagonal distal orifice. The inlet port receives the distal end of the lowermost end of the drip chamber through an uppermost end cover.

A circumferential channel is disposed within the uppermost end of the inlet port, radially adjacent to the distal end of the drip chamber. The circumferential channel has an outer edge which comprises a portion of the upper distal edge of the inlet port. The circumferential channel has an inner edge which is spaced from the side wall of the drip chamber and the uppermost end cover.

Tipping or improper disposition of the drainage bag will cause fluid from the bag to fill the circumferential channel in the uppermost distal portion of the inlet port, if not effectuating reflux of urine into the drip chamber and catheter, into the patient.

The channel retains the fluid so that such an occurrence is detected, and whatever medical attention and corrective action necessary, may occur.

BRIEF DESCRIPTION OF THE DRAWINGS

The objects and advantages of the present invention will become more apparent when viewed in conjunction with the following drawings, in which.

DESCRIPTION OF THE PREFERRED EMBODIMENTS

Figure 1:
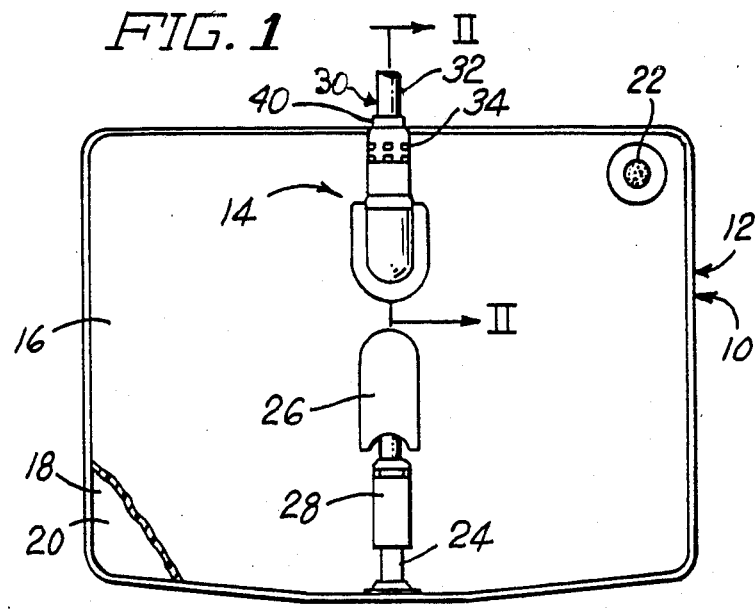
FIG. 1 is a fragmentary front plan view of a collection device of the present invention.

Referring now to the drawings in detail, and particularly to FIG. 1, there is shown a body fluid collection device 10, comprising a container 12 and a connector 14.

The container 12 has a front wall 16 and a back wall 18 of suitable flexible plastic material joined together at their peripheral edges of the front and back walls 16 and 18 to define a chamber 20 in the container 12. The container 12 may have a vent 22 with a bacteria filter of known type to filter bacteria passing from the atmosphere into the container chamber 20.

The container 12 may have a tubular section 24 attached to a lower portion of the container front wall 16 and communicating with the chamber 20, with an outer end of the tubular section 24 being receivable in a pocket 26 on the front wall 16 in a storage position of the tubular section 24. The tubular section 24 may have a suitable clamp 28 which prevents passage of urine through the tubular section 24 when the clamp 28 is closed. When it is desired to drain urine from the container chamber 20, the outer end of the tubular section 24 is removed from the pocket 26, and the clamp 28 may be opened in order to permit passage of urine through the tubular section 24. The clamp 28 is thereafter closed and the tubular section 24 is again inserted into the pocket 26 in the storage position of the tubular section 24.

The connector 14 is hollow, and is in the form of a drip chamber 30 attached to the front wall 16 of the container 12 and communicating with the container chamber 20. As shown, the upper portion of the connector 14 is attached to the lower end of a drainage tube 32, such that the drainage tube 32 provides fluid communication with the distal end of the connector 14. If desired, the connector 14 may have a vent 34 with a bacteria filter of known type to filter bacteria from air passing from the atmosphere into the connector 14 through the vent 34.

Figure 2:
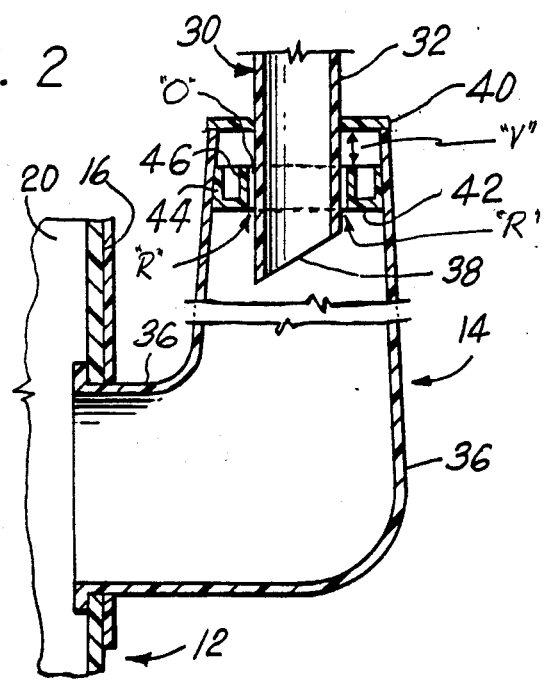
FIG. 2 is a sectional view taken along the lines II—II of FIG. 1.

The drip chamber 30 is of tubular construction and is utilized normally in a vertical orientation with respect to the patient. The drip chamber 30 mates with an inlet port 36 which itself is fixedly attached to the front wall 16 of the container 12. The inlet port 36 is an L-shaped conduit which provides the fluid communication between the drip chamber 30 and the container chamber 20. The drip chamber 30 extends downwardly into the uppermost distal end of the inlet port 36, and terminates inside the inlet port 36 as a diagonally disposed distal orifice 38. The inlet port 36 receives the distal lowermost end of the drip chamber 30, through an uppermost end cover 40, as shown in FIG. 2. The end cover 40 seals the upper end of the inlet port 36, and provides a tight seal with the drip chamber 30.

A circumferential channel 42 is disposed about the uppermost inside edge of the inlet port 36, radially adjacent the drip chamber 30, near its distal end, The circumferential channel 42 has an outer edge 44 which may be attached to or be part of the upper distal edge of the inlet port 36. The circumferential channel 42 has an inner edge 46 which has a radial space "R" from the side wall of the drainage tube 32 defining an annular opening "O" and a vertical space "V" from the uppermost end cover 40. The radial space "R" between the drainage tube 32 and circumferential channel 42 and the vertical space "V" between the channel 42 and the cover 40, permits fluid to enter the channel 42, should the container 12 be tipped too far to the side.

The circumferential channel 42 acts as a reflux indicator means because if the container 12 is lain on its back, and fluid from the container 12 is caused to travel back out the inlet port 36, a residual amount will be retained in the channel 42 because it is continuous around the internal edge of the inlet port 36, and has no means of complete escape therefrom. Further tipping would only make it run to the other side of the channel 42.

The orifice 38 extends into the inlet port 36 beyond the circumferential channel 42, so that urine draining into the inlet port 36 from the drip chamber 30 will not first flow into the channel 42 without the container 12 being tipped improperly.

The inlet port 36 as well as the circumferential channel 42 are preferably made of clear plastic, so that any reflux of urine can readily be determined by visual inspection.

What has thus been shown is a very inexpensive yet reliable reflux indicator for drainage ports of urine containment bags. Their mere presence will make medical personnel more careful to avoid reflux and indicate who is not handling these medical devices properly, when the channel does have some residue of urine therein.

I claim:

1. A reflux indicating device for a urine collection bag which receives urine from a patient, comprising:
    a container having a drainage tube conduit having a proximal end means for securing to patient and a distal end means for securing to said container: said container having a connector comprising a receiving means with distal and proximal end means; said distal end means of said connector in fluid communication with said distal end of said drainage tube; said connector of a generally cylindrical shape having inner and outer wall surfaces; said distal end of said conduit passing through a distally sealed end portion of said receiving means; a reflex indicator means secured to the inner cylindrical wall surface of said connector and spaced from said drainage tube conduit such that upon tipping on to one of the container walls reflux of urine is trapped by said indicator means, said indicator means further comprising a circumferentially disposed channel shaped member means to trap urine upon said tipping.

2. A reflux indicator as recited in claim 1, wherein said receiving means comprises a L-shaped member, having an upper end cover through which said drainage tube extends.

3. A reflux indicator as recited in claim 2, wherein said drainage tube has a lower most distal end comprising a diagonally disposed orifice.

4. A reflux indicator as recited in claim 3, wherein said diagonally disposed orifice of said drainage tube extends down inwardly into said receiving means conduit, beyond said reflux indicator.

5. A reflux indicator as recited in claim 4, wherein said receiving means and said channel are formed from a transparent plastic material.

6. A reflux indicator as recited in claim 4 wherein said channel has an upper edge which has a vertical space between said cover and said outer edge of said channel.

* * * * *